United States Patent
Robinson et al.

(10) Patent No.: US 10,799,306 B2
(45) Date of Patent: Oct. 13, 2020

(54) RECONFIGURABLE END EFFECTOR ARCHITECTURE

(71) Applicant: Intuitive Surgical Operations, Inc., Sunnyvale, CA (US)

(72) Inventors: David W. Robinson, Sunnyvale, CA (US); Gabriel F. Brisson, Sunnyvale, CA (US); Amir Chaghajerdi, Sunnyvale, CA (US); Pushkar Hingwe, Sunnyvale, CA (US); Donald F. Wilson, Jr., Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 319 days.

(21) Appl. No.: 15/774,848

(22) PCT Filed: Nov. 4, 2016

(86) PCT No.: PCT/US2016/060679
§ 371 (c)(1),
(2) Date: May 9, 2018

(87) PCT Pub. No.: WO2017/083201
PCT Pub. Date: May 18, 2017

(65) Prior Publication Data
US 2018/0325611 A1 Nov. 15, 2018

Related U.S. Application Data

(60) Provisional application No. 62/254,154, filed on Nov. 11, 2015.

(51) Int. Cl.
*A61B 34/00* (2016.01)
*A61B 34/35* (2016.01)
(Continued)

(52) U.S. Cl.
CPC .............. *A61B 34/35* (2016.02); *A61B 34/37* (2016.02); *A61B 17/29* (2013.01); *A61B 2034/305* (2016.02)

(58) Field of Classification Search
CPC ......... A61B 34/35; A61B 34/37; A61B 17/29; A61B 2034/305; A61B 34/30; A61B 34/70
See application file for complete search history.

(56) References Cited

U.S. PATENT DOCUMENTS 6,299,624 B1  10/2001  Cuschieri et al.
6,459,926 B1  10/2002  Nowlin et al.
(Continued)

FOREIGN PATENT DOCUMENTS

CN         104434318 A      3/2015
WO    WO-2006124390 A2    11/2006
(Continued)

OTHER PUBLICATIONS

Extended European Search Report for Application No. 16864808.7 dated Jun. 3, 2019, 8 pages.
(Continued)

*Primary Examiner* — Ian Jen
(74) *Attorney, Agent, or Firm* — Kilpatrick Townsend & Stockton LLP

(57) ABSTRACT

Systems and related methods control movement of an end effector. A method of controlling movement of an end effector includes receiving, by a controller, a command to close or open an end effector that includes a first jaw member, a second jaw member, a wrist, and an instrument shaft. In response to the command, the controller controls movement of the end effector to simultaneously move the first jaw member relative to the second jaw member and actuate the wrist to orient the end effector so that at least one of a position and an orientation of a reference aspect of the end effector is substantially maintained in space.

22 Claims, 11 Drawing Sheets

(51) Int. Cl.
*A61B 34/37* (2016.01)
*A61B 34/30* (2016.01)
*A61B 17/29* (2006.01)

(56) References Cited

U.S. PATENT DOCUMENTS

| | | | | |
|---|---|---|---|---|
| 6,770,081 | B1 * | 8/2004 | Cooper | A61B 17/11 606/130 |
| 8,419,766 | B2 * | 4/2013 | Bruewer | A61B 17/29 29/428 |
| 2008/0065100 | A1 | 3/2008 | Larkin | |
| 2010/0331856 | A1 | 12/2010 | Carlson et al. | |
| 2011/0196199 | A1 | 8/2011 | Donhowe et al. | |
| 2011/0218550 | A1 | 9/2011 | Ma | |
| 2011/0290061 | A1 | 12/2011 | Raju | |
| 2012/0179169 | A1 | 7/2012 | Swarup et al. | |
| 2012/0310221 | A1 | 12/2012 | Durant et al. | |
| 2014/0005676 | A1 | 1/2014 | Shelton, IV et al. | |

FOREIGN PATENT DOCUMENTS

| WO | WO-2007111737 A2 | 10/2007 |
|---|---|---|
| WO | WO-2013181507 A1 | 12/2013 |

OTHER PUBLICATIONS

International Search Report and Written Opinion for Application No. PCT/US2016/060679, dated Feb. 22, 2017, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

FIG. 5A
FIG. 5B
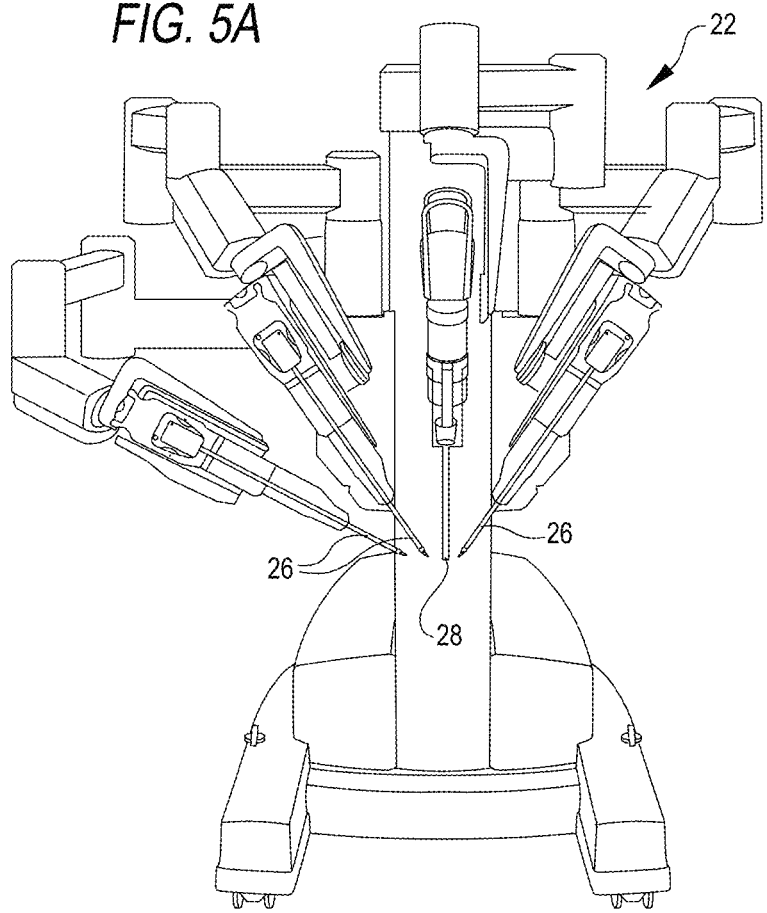
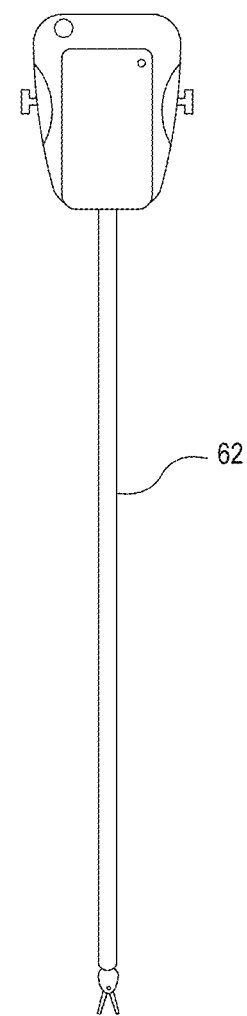

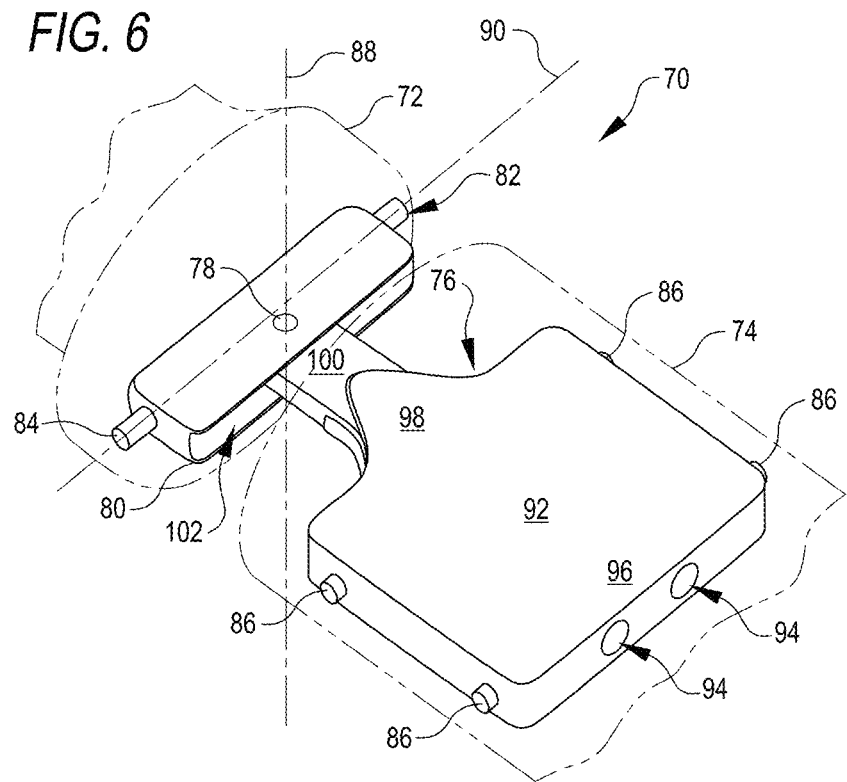

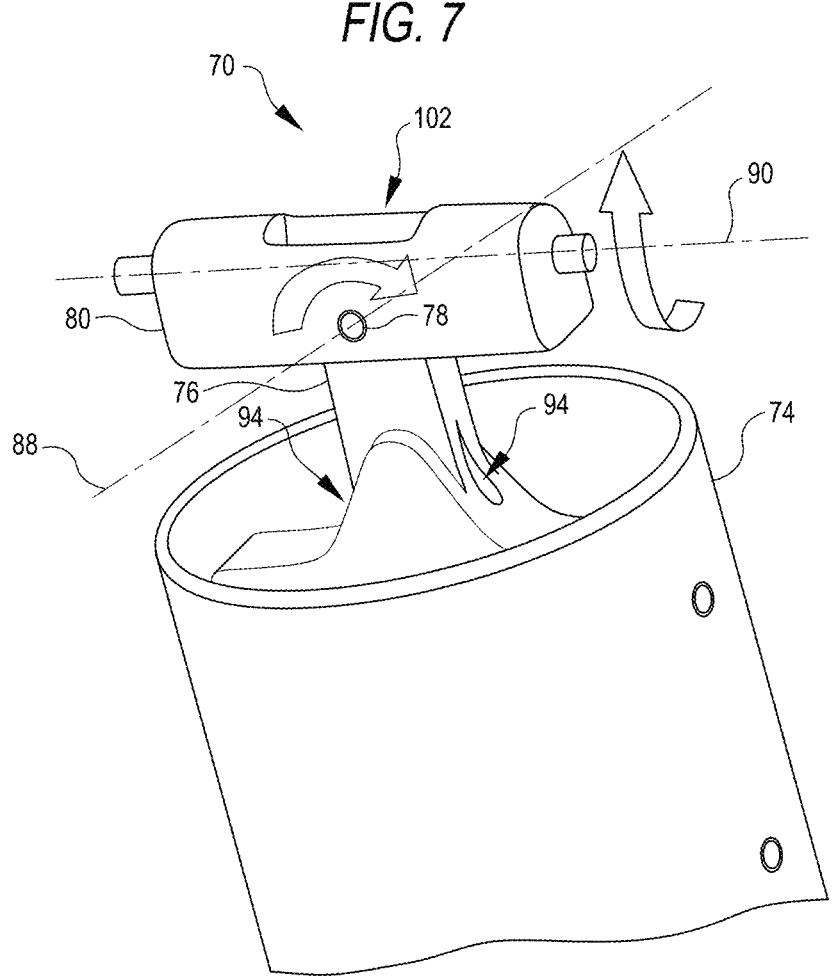

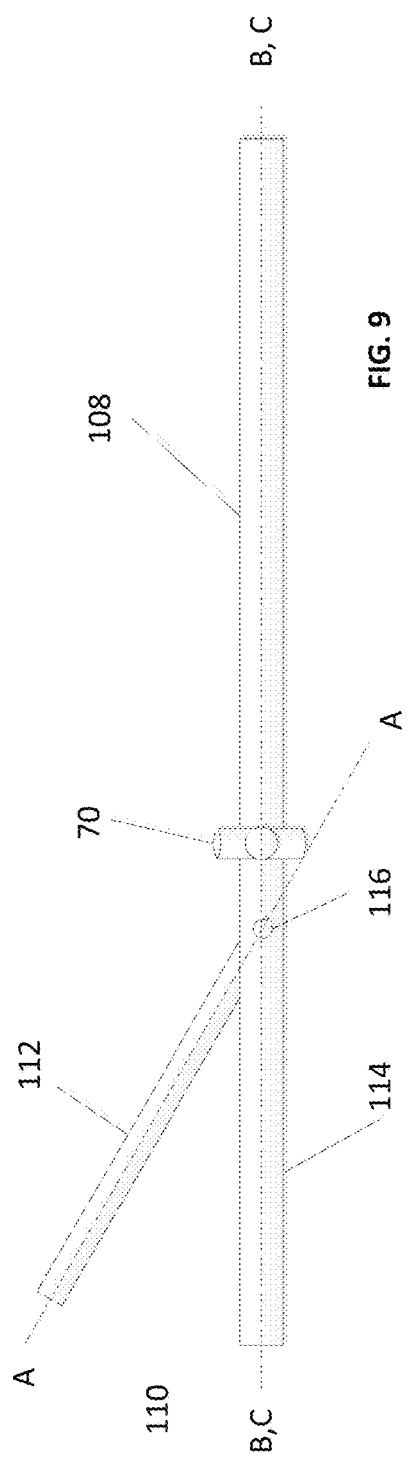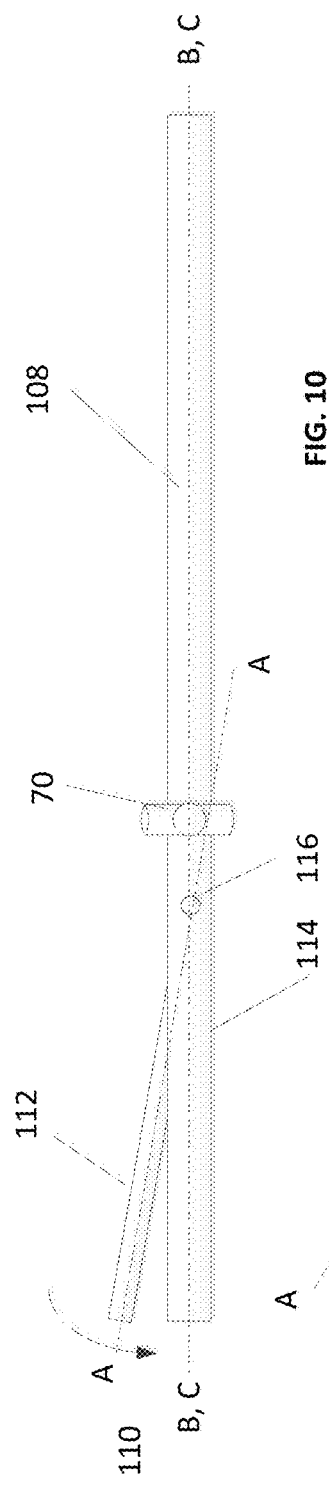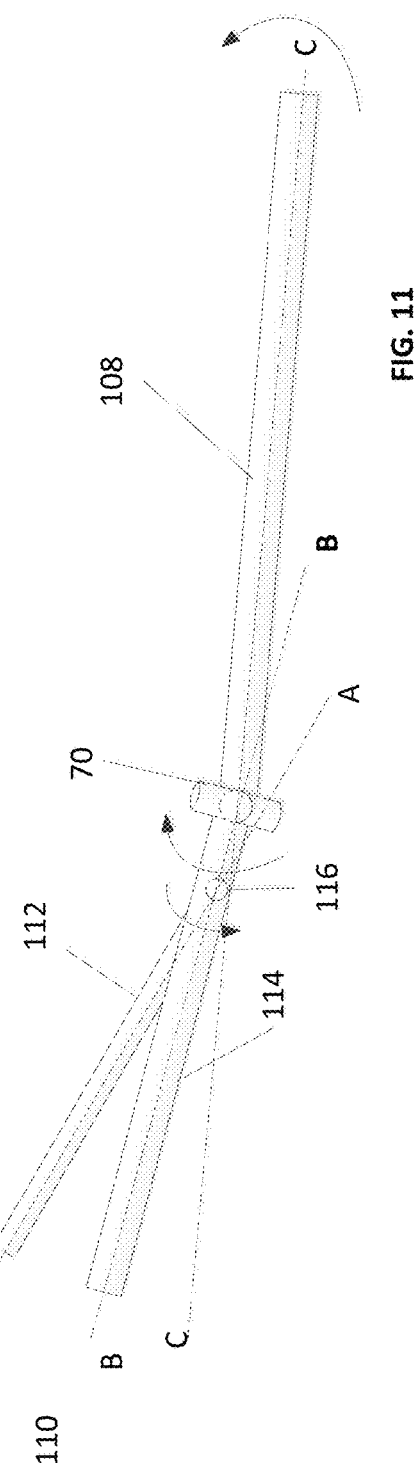

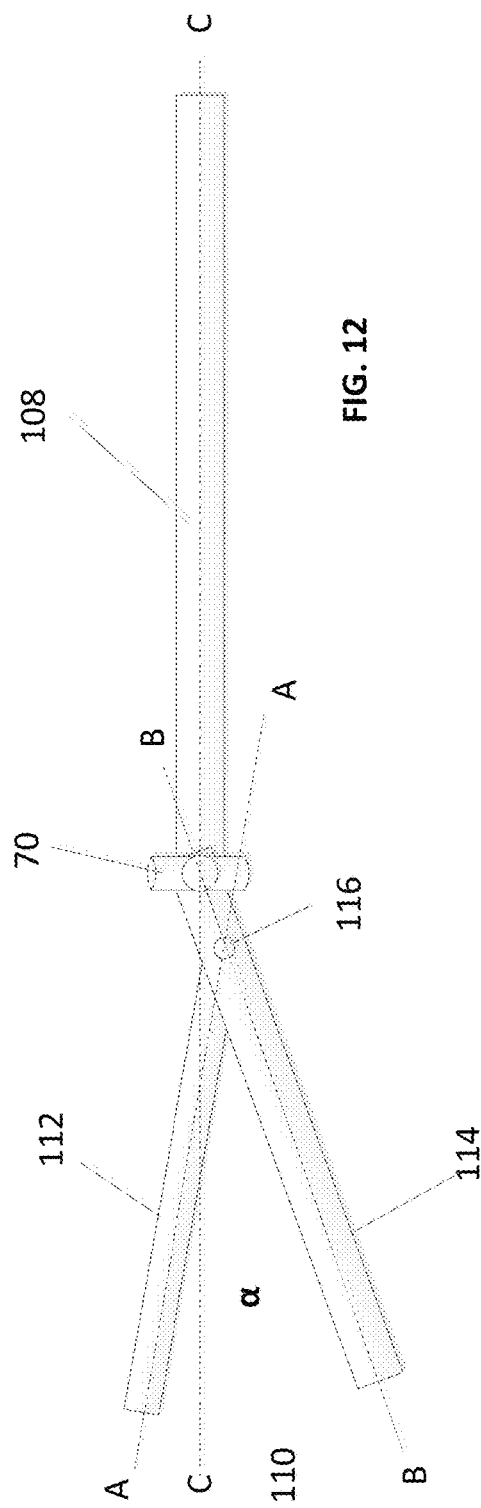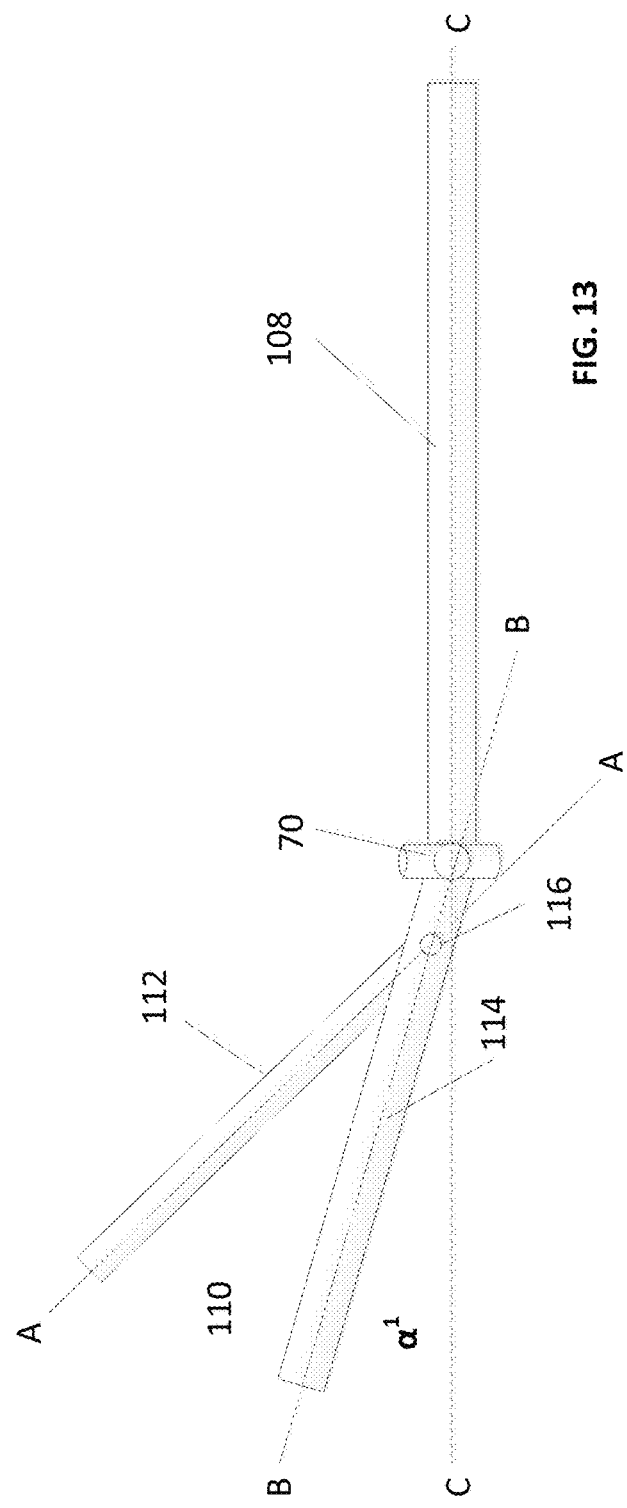

RECONFIGURABLE END EFFECTOR ARCHITECTURE

CROSS-REFERENCES TO RELATED APPLICATIONS

The present application is a U.S. National Stage application of PCT/US2016/060679 filed Nov. 4, 2016, which claims priority to, and the benefit of, U.S. Provisional Patent Application 62/254,154 filed Nov. 11, 2015, the full disclosures which are incorporated herein by reference in their entirety for all purposes.

This application is related to U.S. Pat. No. 8,852,174, entitled "Surgical tool with a two degree of freedom wrist," filed Nov. 12, 2010, and U.S. Pat. No. 9,498,215, entitled "Surgical staple cartridge with enhanced knife clearance," filed Dec. 31, 2013, which are incorporated by reference herein.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive teleoperated surgical systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools. Many of the surgical tools have jaws or other articulatable end effectors that perform various functions for the surgeon, for example, holding or driving a needle, grasping a blood vessel, dissecting tissue, or the like, in response to manipulation of the master input devices. Tools having distal wrist joints allow the surgeon to orient the tool within the internal surgical site, greatly enhancing the freedom with which the surgeon can interact with (and treat) the tissue in real time.

Often, there is only a modest amount of room surrounding the internal surgical site, thereby placing limits on the extent of movement of the surgical tool without undesired contact with surrounding patient tissue. Such movement limits can inhibit a surgeon's ability to perform a desired surgical task. Accordingly, methods and systems having enhanced characteristics for performing surgical tasks in a space-constrained environment are desired.

BRIEF SUMMARY

Systems and methods for controlling movement of an end effector provide for automated combination of multiple actuation inputs to produce a resulting movement of the end effector more suitable to a constrained space than if the actuation inputs are separately employed. For example, with a surgical instrument that includes an end effector that includes jaw members and is mounted to an instrument shaft via a wrist, the wrist and one or more of the jaw members can be actuated simultaneously to reduce movement of a reference aspect of the end effector (e.g., a designated jaw member) in space and thereby inhibit undesired contact with surrounding patient tissue. Accordingly, a surgeon is provided with an automated approach for articulating the end effector in a way compatible with a constrained working space.

Thus, in one aspect, a method of controlling movement of an end effector is provided. The method includes receiving, by a controller, a command to close or open the end effector. The end effector includes a first jaw member joined to a second jaw member by a hinge. The end effector is coupled to an instrument shaft by a wrist that can orient the end effector relative to the instrument shaft. The method includes controlling, by the controller in response to the command, movement of the end effector to simultaneously (a) move the first jaw member relative to the second jaw member, and (b) actuate the wrist to orient the end effector relative to the instrument shaft, wherein at least one of a position and an orientation of a reference aspect of the end effector is substantially maintained in space.

In many embodiments, where the wrist can be reconfigured sufficiently to articulate the end effector relative to the instrument by a requisite amount, the first jaw member can be held substantially stationary during the movement of the end effector. For example, the wrist can be actuated to move the second jaw towards the first jaw member (which can be held stationary) during the closing or opening of the end effector. The first jaw member can be closed against the second jaw member during closing of the end effector.

The first and second jaw members can be configured to open and close in any suitable manner. For example, the first jaw member can be configured to pivot at the hinge to close against the second jaw member and the second jaw member can be configured to not pivot at the hinge. As another example, both the first and second jaw members can be configured to pivot at the hinge relative to an end effector base member that is coupled to the wrist.

The instrument shaft can be articulated as part of the movement of the end effector. For example, the movement of the end effector can include articulating the instrument shaft to move the hinge.

The current configuration of the wrist and/or the instrument shaft can be assessed relative to a corresponding movement limit to determine if sufficient reconfiguration of the wrist and/or instrument shaft is possible to accomplish a desired movement of the end effector. For example, the method can further include determining, by the controller, if a reconfiguration of the wrist and/or the instrument shaft to hold the reference aspect of the end effector stationary during the closing or opening of the end effector exceeds a movement limit for the wrist and/or the instrument shaft. The controller can base the movement of the end effector on a determination that the reconfiguration of the wrist to reorient the end effector relative to the instrument shaft to hold the reference aspect of the end effector stationary during the movement of the end effector exceeds a movement limit for the wrist and/or instrument shaft.

The method can further include employing opening and/or closing the end effector without reconfiguring the wrist and/or articulating the instrument shaft. For example, the method can further include (a) receiving, by the controller, a second command to close or open the end effector; and (b) controlling, by the controller in response to the second command, movement of the end effector to reorient the first jaw member relative to the second jaw member without simultaneously articulating the end effector to hold the reference aspect of the end effector stationary.

The method can include user designation of the reference aspect of the end effector. For example, the method can include receiving, by the controller, an input designating the reference aspect of the end effector.

Any suitable wrist can be employed. For example, the wrist can be reconfigurable to reorient the end effector relative to the instrument shaft about a yaw axis and a pitch axis perpendicular to the yaw axis.

In another aspect, a robotic surgery system is provided. The robotic surgery system includes an end effector, a wrist, an instrument shaft, and a controller. The end effector includes a first jaw member, a second jaw member, and a hinge by which the first jaw member is pivotally coupled to the second jaw member. The end effector is coupled to the wrist. The wrist is reconfigurable to move the end effector relative to the instrument shaft. The controller includes at least one processor and a memory device storing instructions executable by the at least one processor to cause the at least one processor to receive a command to move the first jaw member relative to the second jaw member and, in response to the command, control movement of the end effector to simultaneously (a) move the first jaw member relative to the second jaw member, and (b) actuate the wrist to orient the end effector relative to the instrument shaft, wherein at least one of a position and an orientation of a reference aspect of the end effector is substantially maintained in space. The robotic surgery system can be configured to perform any of the acts of the methods of controlling movement of an end effector described herein.

For a fuller understanding of the nature and advantages of the present invention, reference should be made to the ensuing detailed description and accompanying drawings.

Other aspects, objects and advantages of the invention will be apparent from the drawings and detailed description that follows.

BRIEF DESCRIPTION OF THE DRAWINGS

FIG. 5A is a front view of a patient-side cart of a teleoperated surgical system, in accordance with many embodiments.

FIG. 5B is a front view of a surgical tool.

FIG. 6 is a perspective view of a two degree-of-freedom wrist coupling an end effector body with an instrument shaft, in accordance with many embodiments.

FIG. 7 is a perspective view of the two degree-of-freedom wrist of FIG. 6, illustrating rotational degrees of freedom between an intermediate member of the wrist and a support member of the wrist, and between the intermediate member and the end effector body, in accordance with many embodiments.

FIGS. 9-13 simplified diagrammatic illustration of a surgical assembly according to different modes of operation, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
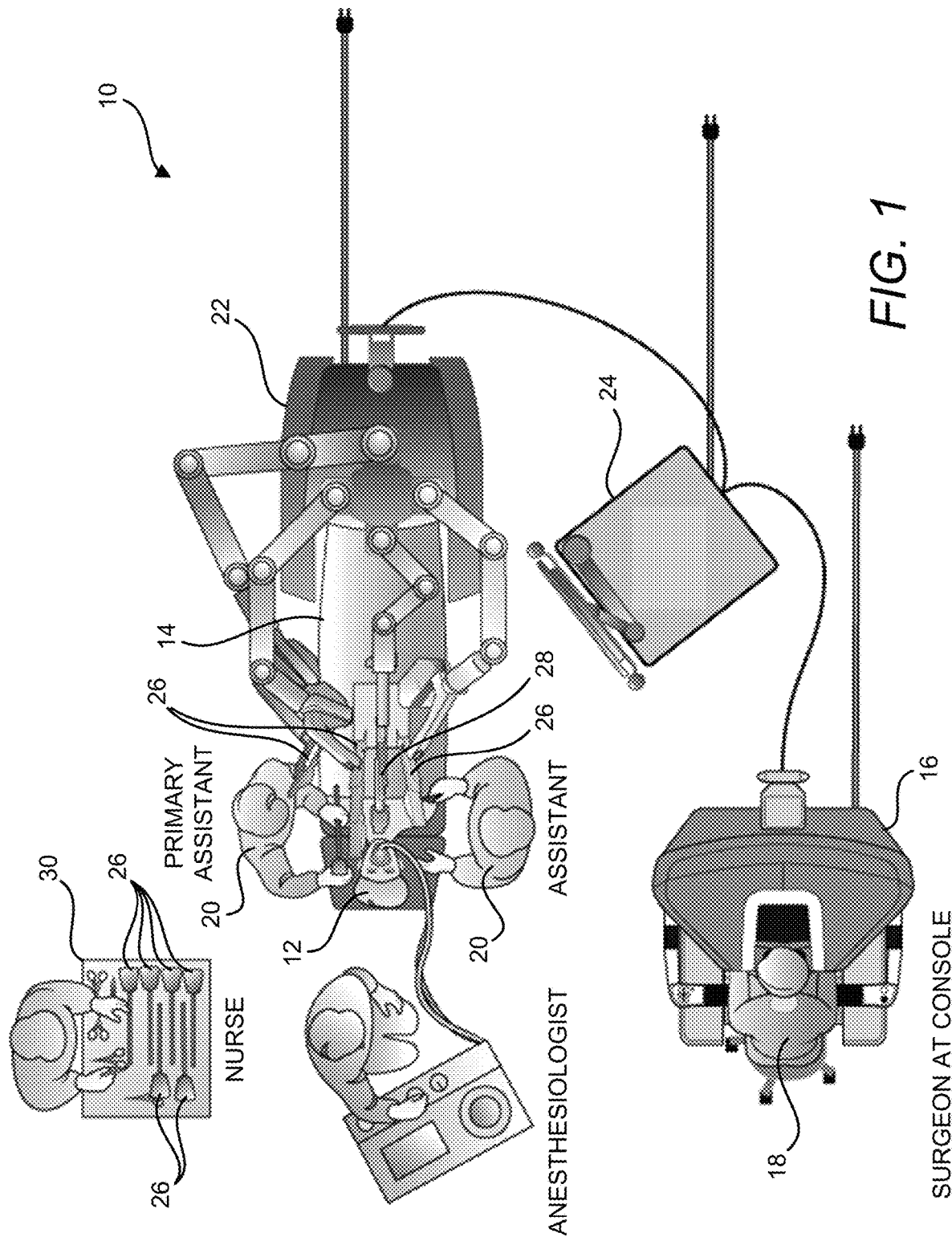
FIG. 1 is a plan view of a minimally invasive teleoperated surgical system being used to perform a surgery, in accordance with many embodiments.

FIG. 1 is a plan view illustration of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient-Side Cart 22, and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient-Side Cart 22 so as to orient the endoscope 28.

The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient-Side Cart 22, and replace it with another tool 26 from a tray 30 in the operating room.

Figure 2:
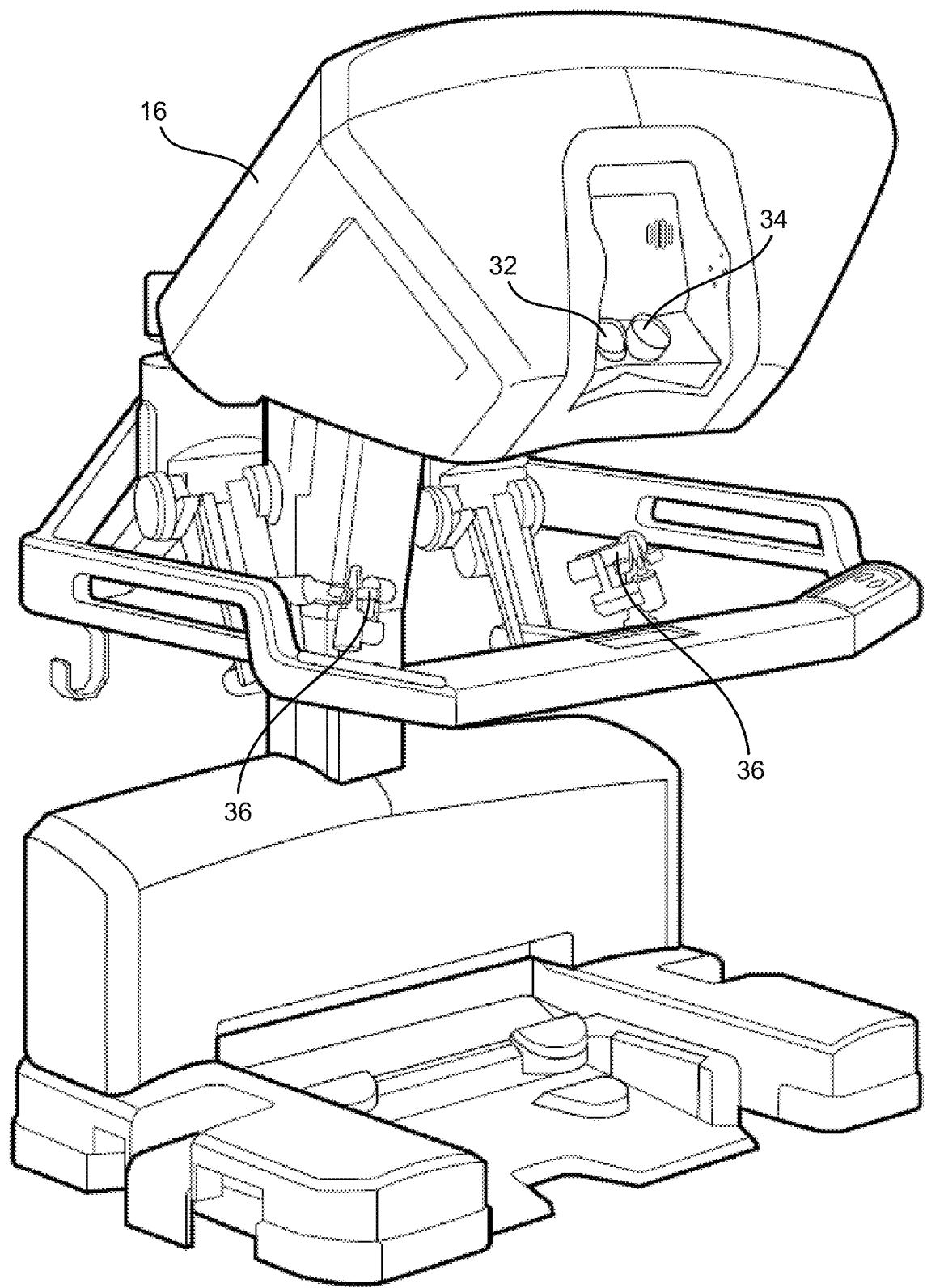
FIG. 2 is a perspective view of a surgeon's control console for a teleoperated surgical system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient-Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
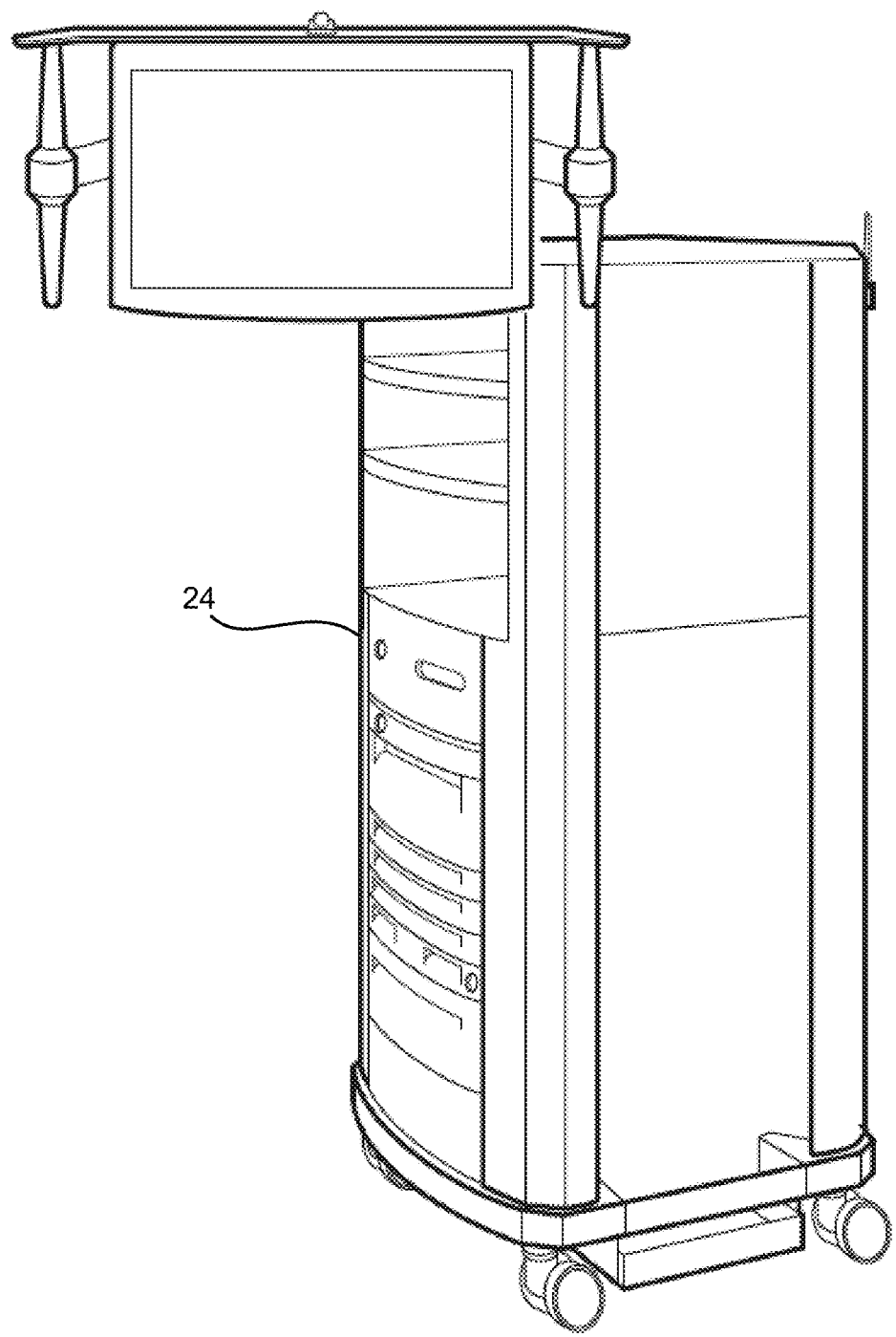
FIG. 3 is a perspective view of a teleoperated surgical system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image-capture device, such as optical aberrations.

Figure 4:
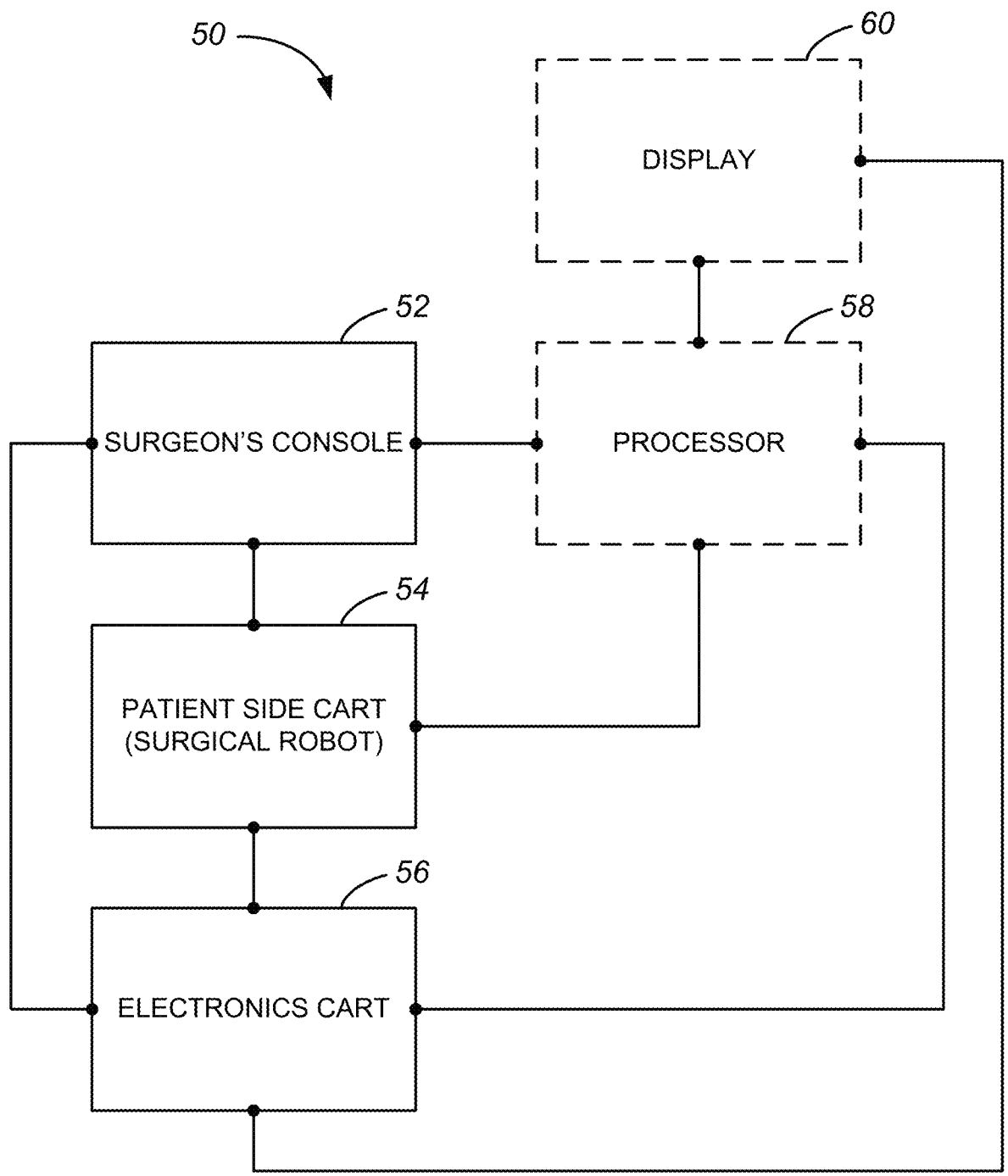
FIG. 4 is a simplified diagrammatic illustration of a teleoperated surgical system, in accordance with many embodiments.

FIG. 4 diagrammatically illustrates a teleoperated surgical system 50 (such as teleoperated surgical system 10 of FIG. 1). As discussed above, a Surgeon's Console 52 (such as Surgeon's Console 16 in FIG. 1) can be used by a Surgeon to control a Patient-Side Cart 54 (such as Patent-Side Cart 22 in FIG. 1) during a minimally invasive procedure. The Patient-Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient-Side Cart 54 can output the captured images for processing outside the Electronics Cart 56. For example, the Patient-Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or any other related images.

FIGS. 5A and 5B show a Patient-Side Cart 22 and a surgical tool 62, respectively. The surgical tool 62 is an example of the surgical tools 26. The Patient-Side Cart 22 shown provides for the manipulation of three surgical tools 26 and an imaging device 28, such as a stereoscopic endoscope used for the capture of images of the site of the procedure. Manipulation is provided by mechanisms having a number of joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

FIG. 6 is a perspective view of a two degree-of-freedom wrist 70 coupling an end effector body 72 with an instrument shaft 74, in accordance with many embodiments. The wrist 70 includes a support member 76, a first hinge point 78, an intermediate member 80, a second hinge point 82, and a third hinge point 84. The support member 76 is fixedly mounted to the instrument shaft 74 via four attachment features 86 (e.g., mechanical fasteners) so as to be positioned within a bore of the instrument shaft 74 as illustrated. The intermediate member 80 is pivotally coupled with the support member 76 for rotation about a first axis 88 via the centrally-located first hinge point 78. The end effector body 72 is pivotally coupled with the intermediate member 80 for rotation about a second axis 90 via the peripherally-located second hinge point 82 and the peripherally-located third hinge point 84. The second hinge point 82 and the third hinge point 84 are coaxial and aligned with the second axis 90. The second axis 90 pivots with the intermediate member about the first axis 88.

The first axis 88 and the second axis 90 can be positioned to provide a compact two degree-of-freedom wrist with desired kinematics and/or spatial characteristics. For example, the first axis 88 and the second axis 90 can be coplanar, and thereby provide a compact wrist member with ball-joint like kinematics. In many embodiments, the first axis 88 and the second axis 90 are separated by a desired distance along an elongate direction of the instrument shaft 74.

Such a separation can be used to approximate and/or match the kinematics of the wrist mechanism to the kinematics of actuation system components used to orient the end effector body 72 relative to the instrument shaft 74 via the two degree-of-freedom wrist. In many embodiments, the first axis 88 and the second axis 90 are separated by a desired distance along the elongate direction of the instrument shaft 74 so as to provide a two degree-of-freedom wrist with a desired combination of compactness and kinematics that approximately match the kinematics of the actuation system components used to orient the end effector body 72 relative to the instrument shaft 74. For example, if a 4 mm separation between the first axis 88 and the second axis 90 would match the kinematics of the actuation system orientation components used, the two degree-of-freedom wrist can be configured with a smaller separation (e.g., 2 mm) so as to provide a more compact wrist. In many embodiments, such a separation distance compromise can be employed without inducing any significant detrimental operating characteristics from not exactly matching the kinematics of the actuation system orientation components used. The first axis 88 and the second axis 90 can be positioned to provide a compact two degree-of-freedom wrist with desired spatial characteristics. For example, the first axis 88 and the second axis 90 can be separated to provide additional space for actuation system components and related attachment features.

The support member 76 provides a transitional fitting between the instrument shaft 74 and the first hinge point 78. The support member 76 includes a rectangular main portion 92 and a cantilevered distal portion 100. The rectangular main portion 92 has a thickness that is less than the inside diameter of the instrument shaft bore, which leaves two adjacent regions of the bore open for the routing of articulation and/or actuation components (not shown). The support-member main portion 92 includes two internal passages 94, which can be used to guide end effector control cables routed within the instrument-shaft bore. The internal passages 94 are routed between a proximal end 96 of the main portion 92 and a distal end 98 of the main portion 92 and are generally aligned with the elongate direction of the instrument shaft 74. As will be discussed further below, in many embodiments, the internal passages 94 are configured to work in conjunction with cable guide surfaces of the intermediate member to inhibit altering control cable tensions during pivoting about the first and second axes by maintaining constant control cable path lengths. The cantilevered distal portion 100 has an attachment lug that receives a single pivot shaft of the first hinge point 78. The use of a single pivot shaft is merely exemplary, and other pivot joint components can be used in place of the first hinge point 78, for example, two pivot pins aligned on the same axis can be used. The support member 76 is configured to place the first hinge point 78 (and therefore the first axis 88) at a desired location relative to the instrument shaft 74 and the end effector body 72, for example, to provide clearance between the end effector body 72 and the instrument shaft 74 necessary for a desired range of reorientation of the end effector body 72 relative to the instrument shaft 74.

The intermediate member 80 provides a transitional fitting between the first hinge point 78, the second hinge point 82, and the third hinge point 84. The intermediate member 80 includes an elongate rectangular main portion that has a thickness that is less than the inside diameter of the instrument shaft bore (e.g., similar to the thickness of main portion 92), which leaves two adjacent regions open for the routing of articulation and/or actuation components (not shown). The intermediate member 80 includes a central slot 102 configured to receive the attachment lug of the support-member distal portion 100. The central slot 102 is configured to accommodate the attachment lug of the distal portion 100 throughout a range of rotation of the intermediate member 80 about the first axis 88. The central slot 102 can also be configured to accommodate end effector control cables (not shown) that are routed through the support-member internal passages 94. The central slot 102 can also include surfaces configured to guide end effector control cables. As will be discussed further below, in many embodiments, the central-slot cable-guiding surfaces are configured to inhibit altering control cable tensions during pivoting about the first and second axes by maintaining substantially constant control cable path lengths. In many embodiments, the central-slot cable guiding surfaces work in conjunction with the internal passages 94 to maintain constant control cable path lengths during pivoting about the first and second axes. The central slot 102 also provides opposing attachment flanges that receive the single pivot shaft of the first hinge point 78. The second hinge point 82 includes a pivot shaft cantilevered from a first end of the intermediate member 80. The third hinge point 84 includes a pivot shaft cantilevered from an opposing second end of the intermediate member 80. The use of cantilevered pivot shafts is merely exemplary, and other suitable pivot joints can be used. In many embodiments, the positions and orientations of the second and third hinge points 82, 84 (and hence the position and orientation of the second axis 90) are selected so as to provide a desired position and orientation of the second axis 90 relative to the first axis 88. For example, in many embodiments, the first and second axes are non-coplanar. In many embodiments, the first and second axes are coplanar. In many embodiments, the position and/or orientation of the second axis 90 relative to the first axis 88 is selected to provide desired kinematics for the movement of the end effector body 72 relative to the instrument shaft 74.

FIG. 7 is a perspective view of the two degree-of-freedom wrist 70 of FIG. 6, illustrating the rotational degree-of-freedom between the intermediate member 80 and the support member 76 about the first axis 88, and the rotational degree-of-freedom between the end effector body (not shown) and the intermediate member 80 about the second axis 90, in accordance with many embodiments. The support member 76 is mounted to the instrument shaft 74 so as to position the first hinge point 78 as a desired location distal from the distal end of the instrument shaft 74, for example, to provide clearance between the end effector body and the instrument shaft so as to provide space for movement of the end effector body. The intermediate-member central slot 102 is open to the side of the intermediate member 80 adjacent to the end effector body so as to accommodate routing of end effector control cables (not shown). From the view direction of FIG. 7, one internal passage 94 of the support member 76 is visible and the other internal passage 94 is hidden from view. In many embodiments, one control cable is routed through each of the two internal passages 94. Each of these two control cables is further routed through the intermediate-member central slot 102, one on each side of the first axis 88.

Figure 8:
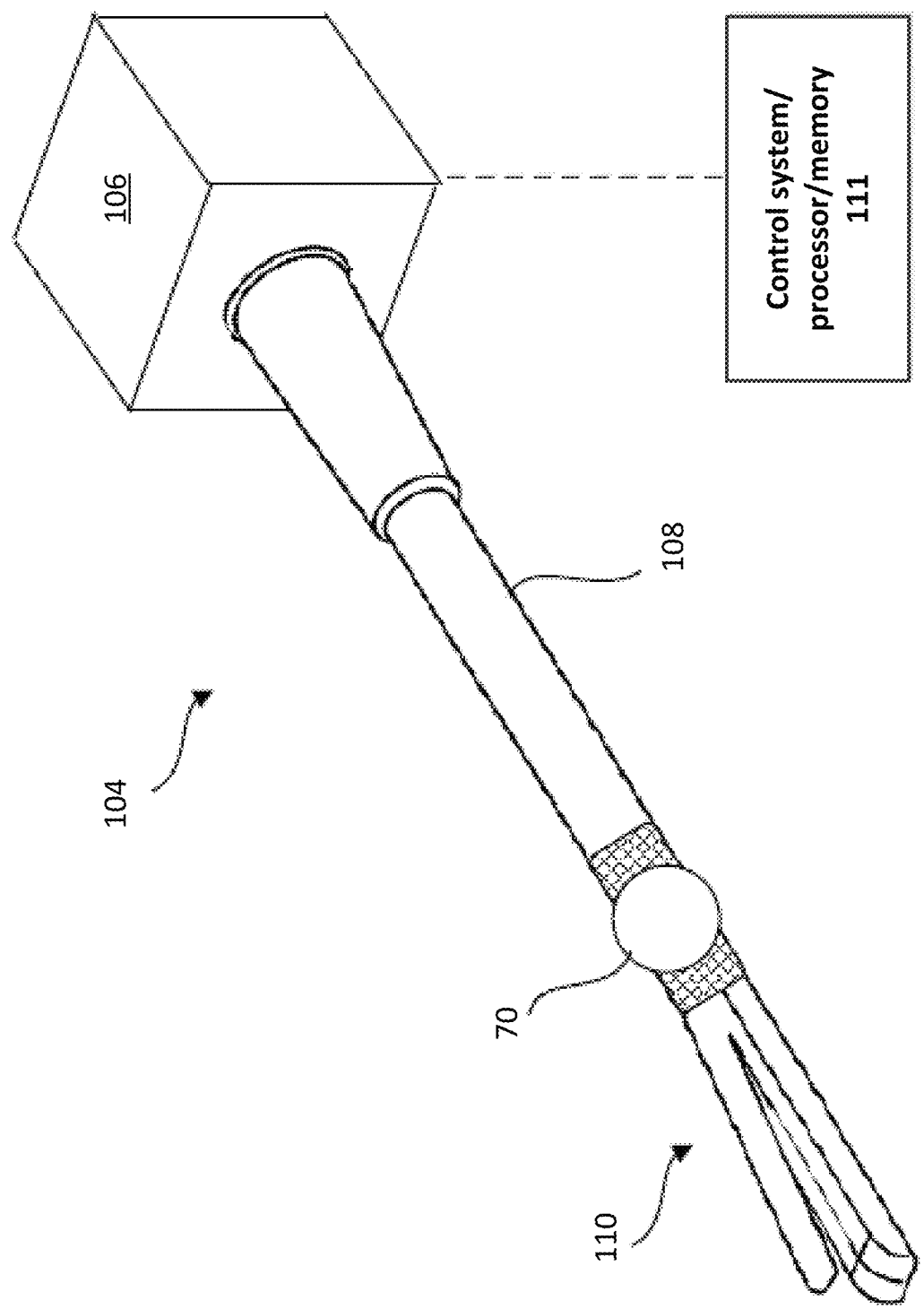
FIG. 8 is a simplified diagrammatic illustration of a surgical assembly, in accordance with many embodiments.

FIG. 8 is a simplified diagrammatic illustration of a tool assembly 104 having the two degree-of-freedom wrist 70, in accordance with many embodiments. The tool assembly 104 includes a proximal actuation assembly 106, a main shaft 108, an articulated end effector base of an end effector 110, and the two degree-of-freedom wrist 70. In many embodiments, the proximal actuation assembly 106 is operatively coupled with the end effector base so as to selectively reorient the end effector base relative to the main shaft 108 in two dimensions, and is operatively coupled with the end effector 110 so as to articulate one or more end effector features relative to the end effector base. A variety of actuation components can be used to couple the actuation assembly 106 with the end effector 110, for example, control cables, cable/hypotube combinations, drive shafts, pull rods, and push rods. In many embodiments, the actuation components are routed between the actuation assembly 106 and the end effector 110 through a bore of the main shaft 108. Details of such connections can be found at previously incorporated U.S. Pub. No. US 20140183244.

The tool assembly 104 can be configured for use in a variety of applications, for example, as a hand-held device with manual and/or automated actuation used in the proximal actuation mechanism 106. As such, the tool assembly 104 can have applications beyond minimally invasive robotic surgery, for example, non-robotic minimally invasive surgery, non-minimally invasive robotic surgery, non-robotic non-minimally invasive surgery, as well as other applications where the use of a two degree-of-freedom wrist would be beneficial. The wrist 70 can be coupled to a variety of end effectors, including, but not limited to, surgical stapling devices, such as the devices disclosed at previously incorporated U.S. Pub. No. US 20140183244.

The tool assembly 104 is electronically coupled to a control system 111, which can include at least one processor for controlling the tool assembly and memory for storing non-transient instructions executable by the at least one processor to perform the method acts described herein. The control system 111 can be located in any suitable location, such as on any part of the tool assembly, or the control system 111 can be part of a sub-system of the patient side cart 22/54 or surgeon console 16. Generally, the control system 111 is configured to execute instructions for carrying out the methods disclosed herein.

FIG. 9 is a simplified view of the tool assembly 104. The end effector 110 includes an upper jaw portion 112 connected to a lower jaw portion 114 by a hinge 116. The upper jaw 112 can open and close with respect to the lower jaw portion 114 by rotation of the upper jaw 112 at the hinge 116. In this embodiment, the lower jaw portion 114 cannot actuate at the hinge 116, because the lower jaw portion 114 carries the hinge. However, in other embodiments, both jaw portions can actuate at the hinge 116. The lower jaw portion 114 includes one or more mechanisms for actuating the upper jaw portion 112 at hinge 116. Details of such mechanisms can be found at previously incorporated U.S. Pub. No. US 20140183244. The hinge 116 is spatially separated from the wrist 70. As such, the lower jaw portion 114 can pitch and yaw at wrist 70 while carrying the upper jaw portion 112.

FIG. 10 shows a first mode of operation of the tool assembly 104 for actuation of the upper jaw portion 112 to the lower jaw portion 114. In operation, the upper jaw 112 on axis A-A is moved relatively towards the lower jaw 114 on axis B-B. For simplicity, axis C-C of the main shaft is shown to be co-linear with axis B-B, however, this is not required. Other operations of the tool assembly 104 can occur during this time, such as the rotation of the shaft 108 and movement of the lower jaw 114 at wrist 70, however generally axis B-B can be held stationary in space for more critical surgical operations of the end effector 110.

FIG. 11 shows a second mode of operation of the tool assembly 104 for actuation of the upper jaw portion 112 to the lower jaw portion 114. In some cases, the view of the surgeon with respect to a camera may make it desirable for the axis A-A of the upper jaw portion 112 to remain relatively stationary with respect to the patient while the upper jaw portion 112 is actuated at the hinge 116 to close against the lower jaw portion 114. Hence, in the second mode of operation, the lower jaw portion 114 can be reoriented and/or repositioned (e.g., via articulation of the wrist 70) as the upper jaw portion 112 is actuated towards the lower jaw portion 114 to provide stationary positioning of axis A-A in space. The actuation of the lower jaw portion 114 can be accomplished via articulation of the wrist 70 and/or the instrument shaft 108 so that the upper jaw portion 112 remains stationary in space while the lower jaw portion 114 is reoriented relative to the upper jaw portion 112.

In the illustrated embodiment, due to the spatial separation between the wrist 70 and the hinge 116, the position of the upper jaw portion 112 and axis A-A in space may not always be precisely maintained, but can be substantially maintained sufficient for the purposes of the surgeon. Put another way, the position of the upper jaw portion 112 in space may vary somewhat, but can vary substantially less than how much the lower jaw portion 114 is moved in space. This may be due to kinematic limitations of the side-cart 22, or in some cases physical barriers (such as an abdomen wall) that prevent desired manipulation due to potential collision with aspects of the side-cart 22 and/or tool assembly 104. However, in some cases, movement of the shaft 108 in space can be performed to move the position of the wrist 70 while actuation of the jaw portions occurs to help maintain precise position of axis A-A and hinge 116 in space.

As shown at FIG. 5A, one or more moveable aspects of the arm of patient side cart 22 can be manipulated to maintain precise location of the upper jaw portion 112 and axis A-A in surrounding space. In some cases, this can require coordinated motion of up to 7 axes of motion of the arm holding the tool assembly 104. Examples of such arms and axes of motion are disclosed in U.S. Pat. No. 7,594,912, and U.S. Pub. No. 20130325032, which are incorporated by reference herein. Due to the aforementioned special separation of the wrist 70 and the hinge 116, the wrist 70 as shown at FIG. 11 can be moved downward via control of the patient side cart 22 and manipulation of several moveable aspects of the arm holding the tool assembly 104 to precisely maintain position of the upper jaw portion 112.

The second mode of operation shown at FIG. 11 differs from the first mode of operation as depicted at FIG. 10 in that articulation of the upper jaw portion 112 relative to the lower jaw portion 114 is accompanied with simultaneous articulation of the wrist 70 so that the upper jaw portion 112 is held substantially stationary in space. In contrast, in the first mode of operation depicted in FIG. 10, the articulation of the upper jaw portion 112 relative to the lower jaw portion 114 occurs independently of articulation of the wrist 70 so that the upper jaw portion 112 changes position in space. The second mode of operation can be employed for controlling operation of any suitable surgical tool. Additionally, any suitable aspect of the tool can be selected to be held stationary during actuation of the upper jaw portion 112 relative to the lower jaw portion 114.

The second mode of operation can be enacted in a number of different manners, for example, the second mode of operation may be an option provided at console 16. In other embodiments, the second mode of operation is made default as a result of a designated procedure, a physical selection switch located on the end effector 110, or an electronic identifier located on a stapler cartridge (or other tool insert) that is fed into the end effector 110 (the cartridge can be color coded, such as color based, for purposes of identification to the user). In other embodiments, the second mode of operation is enacted when the wrist 70 is articulated to a certain position or angle. In other embodiments, the angular limits of the second mode of operation can be adjusted by the user. In addition, while the upper jaw portion 112 is used in these examples as a reference aspect of the end effector that is held stationary, any suitable aspect of the tool assembly 104 can be used instead. For example, a virtual reference axis, such as an axis between the opened angle between the upper jaw portion 112 and lower jaw portion 114, can be selected and held stationary. The virtual reference axis can be represented by a suitable display element on the console 16. As another example, any suitable portion of the tool can be selected and held stationary. The user before or during operation of the tool assembly 104 can optionally select such a reference axis or object to be held stationary during articulation of the tool assembly 104. Suitable selectable reference aspects of the end effector can be provided visually on the console 16 as a list of real-time selectable options.

FIG. 12 shows an example of the lower jaw portion 114 being at a mechanical limit with respect to the wrist 70. Here, the angle α between axis B-B and axis C-C is at a maximum due to mechanical limitations of the wrist 70 and lower jaw 114. This position does not impede the first mode operation shown at FIG. 10, because the upper jaw portion 112 is free to pivot at hinge 116. This position also does not impede the second mode of operation shown at FIG. 11, because the relative movement required by the lower jaw portion 114 is not impeded by the wrist 70 because the angle α is not required to increase, but only decrease which is not limited here.

FIG. 13 shows another example of the lower jaw portion 114 being at a mechanical limit with respect to the wrist 70. Here, the angle $α^1$ between axis B-B and axis C-C is at a maximum due to mechanical limitations of the wrist 70 and lower jaw 114. This position does not impede the first mode operation shown at FIG. 10, because the upper jaw portion 112 is free to pivot at hinge 116. However, this position does impede the second mode of operation shown at FIG. 11, because the relative movement required by the lower jaw portion 114 is impeded by the wrist 70 because the angle $α^1$ cannot be increased further.

In such situations where the second mode of operation is desired, a number of alternative modes can occur. In some embodiments, in the second mode of operation, pitch and yaw of the lower jaw portion 114 is limited electronically to be ($α^1$-x), such that the angle $α^1$ can be increased if necessary up to an amount of x, where x is the minimum angle to provide the second mode of operation. In other embodiments, the pitch and yaw of the lower jaw portion 114 is not limited, and the console 16 is configured to provide an indication that the second mode of operation is not available to the surgeon. And in other embodiments, the pitch and yaw of the lower jaw portion 114 is not limited, and movement of the end effector 110 automatically switches to the first mode of operation in such a situation. In some embodiments, the angle $α^1$ may not be at a hard stop, but yet is not at a proper location to provide full operation of the second mode of operation. In such cases, the second mode of operation can be enacted up to the maximum amount as provided by the angle $α^1$ and then, the first mode of operation can be enacted to finish closing the jaw portions. Thus, a certain portion of the motion can be performed by the upper jaw portion 112 and a certain portion of the motion can be performed by the lower jaw portion 114. In some embodiments, if only a small portion of the motion can be accomplished via the second mode of operation, switching to the first mode of operation can be performed automatically.

Figure 14:
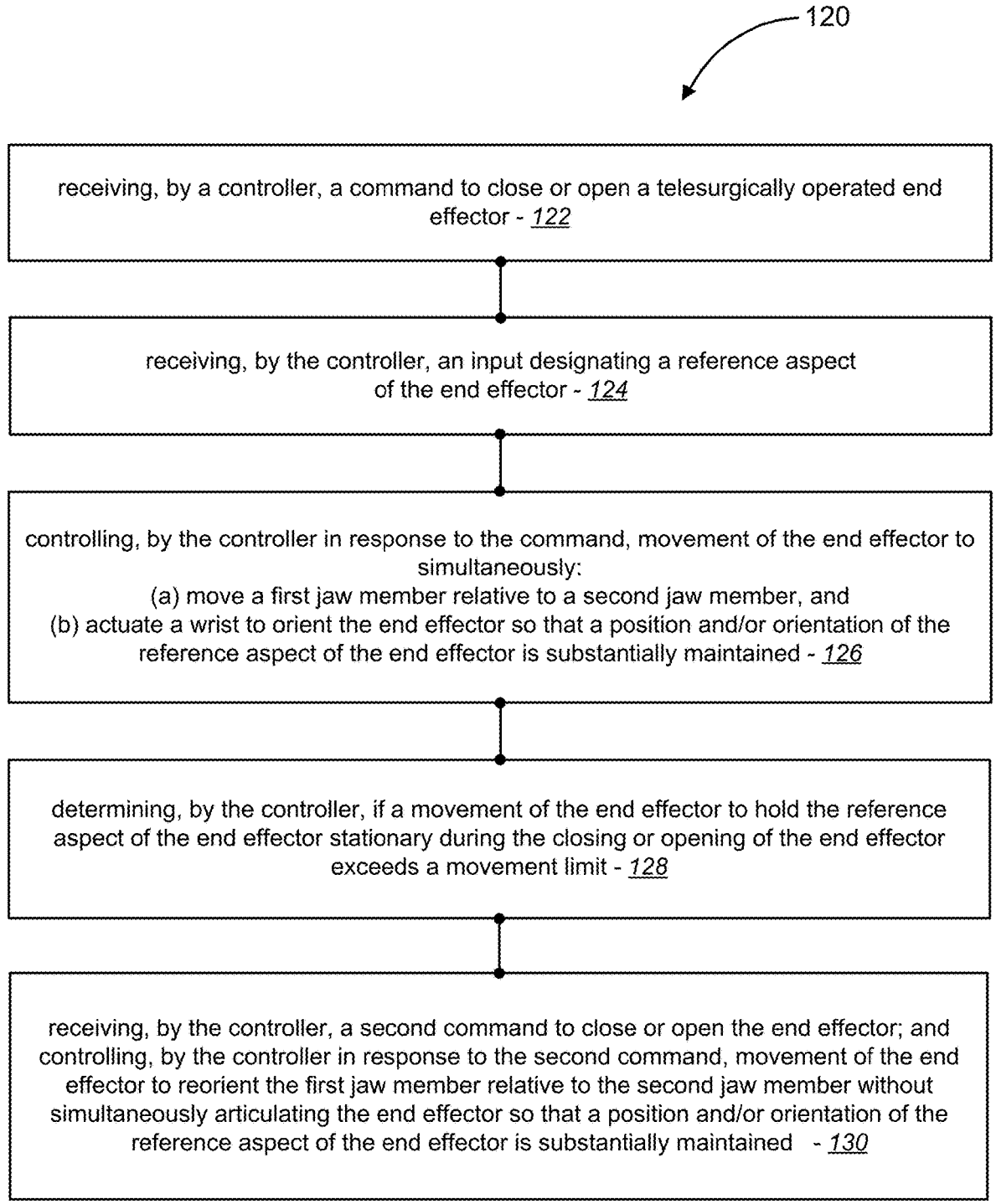
FIG. 14 is a simplified flow diagram of a method of operating an end effector, in accordance with many embodiments.

FIG. 14 illustrates a method 120 for operating a tool, such as tool assembly 104, having an end effector, such as end effector 110. The method 120 can be practiced using any suitable surgical system, such as the surgical systems described herein. In many embodiments, the method 120 is performed using at least one processor, such as the processor of control system 111.

The method 120 includes receiving, by a controller, a command to close or open an end effector (act 122). Any suitable end effector can be used. For example, the end effector can include a first jaw member joined to a second jaw member by a hinge. The end effector can be coupled to an instrument shaft by a wrist that is reconfigurable to articulate the end effector relative to the instrument shaft and thereby reorient and/or reposition the end effector relative a patient. In some embodiments, the instrument shaft can also be articulated to reorient and/or reposition the end effector in space.

The method 120 can include receiving, by the controller, an input designating a reference aspect of the end effector (act 124). Any suitable reference aspect of the end effector, including any suitable physical aspect or virtual aspect such as the reference aspects described herein, can be designated by a user and a corresponding input provided to the controller. Alternatively, a default reference aspect of the end effector can be used. The reference aspect of the end effector can also be selected by the controller based any suitable known status information, such as the current orientation and/or position of the end effector. For example, the current orientation and/or position of the end effector in space can be used to select the reference aspect that is located closest to an adjacent tissue of the patient so as to inhibit undesired contact between the end effector and the adjacent tissue of the patient during the closing or opening of the end effector.

The method 120 further includes controlling, by the controller in response to the command, articulation of the end effector to simultaneously (a) move a first jaw member relative to a second jaw member, and (b) actuate the wrist to orient the end effector relative to the instrument shaft so that a position and/or orientation of the reference aspect of the end effector in space is substantially maintained (act 126). Any suitable simultaneous articulation of the end effector can be used. For example, the wrist can be reconfigured to articulate the end effector relative to the instrument shaft so that the reference aspect of the end effector is held substantially stationary while the first jaw member is reoriented relative to the second jaw member. Additionally, the instrument shaft can be articulated, either alone or in combination with articulation of the wrist, to orient the end effector in space so that the reference aspect of the end effector is held substantially stationary while the first jaw member is moved relative to the second jaw member.

The method 120 can include determining, by the controller, if movement of the end effector to hold the reference aspect of the end effector stationary during the closing or opening of the end effector exceeds a movement limit (act 128). For example, a reconfiguration of the wrist and/or instrument shaft that can be used to produce the movement of the end effector to hold the reference aspect of the end effector stationary during the closing or opening of the end effector can be compared with a remaining available reconfiguration of the wrist and/or instrument shaft. If the controller determines that the available reconfiguration from the current configuration of the wrist and/or instrument shaft is sufficient to hold the reference aspect of the end effector stationary throughout the closing or opening of the end effector, the controller can proceed with controlling articulation of the end effector so as to hold the reference aspect of the end effector stationary throughout the closing or opening of the end effector. If the controller determines that the available reconfiguration from the current configuration of the wrist and/or instrument shaft is insufficient to hold the reference aspect of the end effector stationary throughout the closing or opening of the end effector, the controller can proceed with controlling articulation of the end effector so as to hold the reference aspect of the end effector stationary throughout a corresponding portion of the closing or opening of the end effector.

Additionally, the controller can be configured to enable closing or opening the end effector without simultaneously articulating the end effector to hold the reference aspect of the end effector stationary throughout the closing or opening of the end effector. For example, the method 120 can include receiving, by the controller, a second command to close or open the end effector. In response to receiving the second command, the controller can control articulation of the end effector to reorient the first jaw member relative to the second jaw member without simultaneously articulating the end effector (e.g., via articulation of the wrist and/or instrument shaft) so that a position and/or orientation of the reference aspect of the end effector in space is substantially maintained (act 130).

Other variations are within the spirit of the present invention. The various aspects, embodiments, implementations or features of the described embodiments can be used separately or in any combination. Various aspects of the described embodiments associated with operation of surgical tools can be implemented by software, hardware or a combination of hardware and software. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of controlling movement of an end effector, the method comprising:
   receiving, by a controller, a command to close or open the end effector, the end effector including a first jaw member joined to a second jaw member by a hinge, the end effector being coupled to an instrument shaft by a wrist that can orient the end effector relative to the instrument shaft; and
   controlling, by the controller in response to the command, movement of the end effector to simultaneously
      move the first jaw member relative to the second jaw member, and
      actuate the wrist to orient the end effector relative to the instrument shaft,
      wherein at least one of a position and an orientation of a reference aspect of the end effector is substantially maintained in space.

2. The method of claim 1, wherein the first jaw member is held substantially stationary in space during the movement of the end effector.

3. The method of claim 1, wherein the second jaw member is moved towards the first jaw member during the movement of the end effector.

4. The method of claim 1, wherein the first jaw member is closed against the second jaw member during the movement of the end effector.

5. The method of claim 1, wherein:
   the first jaw member is configured to pivot at the hinge to close against the second jaw member; and
   the second jaw member is not configured to pivot at the hinge.

6. The method of claim 1, wherein the movement of the end effector comprises articulating the instrument shaft to move the hinge.

7. The method of claim 1, further comprising determining, by the controller, if a reconfiguration of the wrist to reorient the end effector relative to the instrument shaft to hold the reference aspect of the end effector stationary during the movement of the end effector exceeds a movement limit for the wrist.

8. The method of claim 7, wherein the controller bases the movement of the end effector on a determination that the reconfiguration of the wrist to reorient the end effector relative to the instrument shaft to hold the reference aspect of the end effector stationary during the movement of the end effector exceeds a movement limit for the wrist.

9. The method of claim 1, further comprising:
   receiving, by the controller, a second command to close or open the end effector; and
   controlling, by the controller in response to the second command, movement of the end effector to pivot the first jaw member about the hinge so as to reorient the first jaw member relative to the second jaw member while holding the second jaw member stationary.

10. The method of claim 1, further comprising receiving, by the controller, an input designating the reference aspect of the end effector.

11. The method of claim 1, wherein the wrist is reconfigurable to reorient the end effector relative to the instrument shaft about a yaw axis and a pitch axis perpendicular to the yaw axis.

12. A robotic surgery system comprising:
a robotic arm including an end effector, a wrist, and an instrument shaft having a distal end coupled to the wrist; the end effector including a first jaw member, a second jaw member, and a hinge by which the first jaw member is pivotally coupled to the second jaw member; the end effector being coupled to the wrist; the wrist being reconfigurable to reorient the end effector relative to the instrument shaft;
a controller for operating the robotic arm, the controller including at least one processor and a memory device storing instructions executable by the at least one processor to cause the at least one processor to
receive a command to reorient the first jaw member relative to the second jaw member; and
in response to the command, control movement of the end effector to simultaneously
move the first jaw member relative to the second jaw member, and
actuate the wrist to orient the end effector relative to the instrument shaft,
wherein at least one of a position and an orientation of a reference aspect of the end effector is substantially maintained in space.

13. The system of claim 12, wherein the first jaw member is held substantially stationary during the movement of the end effector.

14. The system of claim 12, wherein the second jaw member is moved towards the first jaw member during the movement of the end effector.

15. The system of claim 12, wherein the first jaw member is closed against the second jaw member during the movement of the end effector.

16. The system of claim 12, wherein:
the first jaw member is configured to pivot at the hinge to close against the second jaw member; and
the second jaw member is not configured to pivot at the hinge.

17. The system of claim 12, wherein the movement of the end effector comprises articulating the instrument shaft to move the hinge.

18. The system of claim 12, wherein the controller is configured to determine if a reconfiguration of the wrist to reorient the end effector relative to the instrument shaft to hold the reference aspect of the end effector stationary during the movement of the end effector exceeds a movement limit for the wrist.

19. The system of claim 18, wherein the controller bases the movement of the end effector on a determination that the reconfiguration of the wrist to reorient the end effector relative to the instrument shaft to hold the reference aspect of the end effector stationary during the movement of the end effector exceeds a movement limit for the wrist.

20. The system of claim 12, wherein the memory device stores instructions executable by the at least one processor to cause the at least one processor to:
receive a second command to close or open the end effector; and
in response to the second command, control movement of the end effector to reorient the first jaw member relative to the second jaw member while holding the second jaw member stationary.

21. The system of claim 12, wherein the memory device stores instructions executable by the at least one processor to cause the at least one processor to receive an input designating the reference aspect of the end effector.

22. The system of claim 12, wherein the wrist is reconfigurable to reorient the end effector relative to the instrument shaft about a yaw axis and a pitch axis perpendicular to the yaw axis.

* * * * *